(12) United States Patent
Liu et al.

(10) Patent No.: US 11,691,138 B2
(45) Date of Patent: Jul. 4, 2023

(54) $CU_y$/$MMGO_x$ INTERFACIAL CATALYST FOR SELECTIVE ALKYNE HYDROGENATION AND ITS PREPARATION METHOD

(71) Applicant: Beijing University of Chemical Technology, Beijing (CN)

(72) Inventors: Yanan Liu, Beijing (CN); Junting Feng, Beijing (CN); Fengzhi Fu, Beijing (CN); Dianqing Li, Beijing (CN); Yufei He, Beijing (CN)

(73) Assignee: Beijing University of Chemical Technology, Beijing (CN)

( * ) Notice: Subject to any disclaimer, the term of this patent is extended or adjusted under 35 U.S.C. 154(b) by 58 days.

(21) Appl. No.: 17/335,019

(22) Filed: May 31, 2021

(65) Prior Publication Data
US 2022/0234036 A1 Jul. 28, 2022

(30) Foreign Application Priority Data
Jan. 26, 2021 (CN) .......................... 202110110149.5

(51) Int. Cl.
| | | |
|---|---|---|
| *B01J 37/03* | (2006.01) | |
| *B01J 23/78* | (2006.01) | |
| *B01J 37/02* | (2006.01) | |
| *B01J 37/06* | (2006.01) | |
| *B01J 37/08* | (2006.01) | |
| *B01J 37/16* | (2006.01) | |
| *C07C 5/09* | (2006.01) | |

(52) U.S. Cl.
CPC ............ *B01J 37/035* (2013.01); *B01J 23/78* (2013.01); *B01J 37/0236* (2013.01); *B01J 37/06* (2013.01); *B01J 37/08* (2013.01); *B01J 37/16* (2013.01); *C07C 5/09* (2013.01)

(58) Field of Classification Search
CPC ...... B01J 37/035; B01J 23/78; B01J 37/0236; B01J 37/06; B01J 37/08; B01J 37/16; B01J 23/8472; B01J 23/86; B01J 23/72; B01J 23/745; C07C 5/09

USPC .................................. 502/328, 331, 312, 316
See application file for complete search history.

(56) References Cited

FOREIGN PATENT DOCUMENTS

| | | | | | |
|---|---|---|---|---|---|
| CN | 102616749 | A | * | 8/2012 | ............. C01B 13/14 |
| CN | 103301840 | A | * | 9/2013 | ............. B01J 23/75 |
| CN | 103464159 | A | * | 12/2013 | ............. B01J 23/745 |
| CN | 112916010 | A | * | 6/2021 | ............. B01J 23/78 |
| WO | WO-9708101 | A1 | * | 3/1997 | ................ C02F 1/72 |
| WO | WO-2018094078 | A1 | * | 5/2018 | ............. B01J 23/002 |

OTHER PUBLICATIONS

Hong Yi et al., "Coating Pd/Al2O3 catalysts with FeOx enhances both activity and selectivity in 1,3-butadiene hydrogenation." Chinese Journal of Catalysis 38, pp. 1581-1587. (Year: 2017).*
Qian Wang et al., "Interfacial Structure-Determined Reaction Pathway and Selectivity for 5-(Hydroxymethyl)furfural Hydrogenation over Cu-Based Catalysts." ACS Catalysis, 10, pp. 1353-1365. (Year: 2020).*

* cited by examiner

*Primary Examiner* — Patricia L. Hailey
(74) *Attorney, Agent, or Firm* — Houtteman Law LLC

(57) ABSTRACT

$Cu_y$/$MMgO_x$ interfacial catalyst for selective alkyne hydrogenation and its preparation method are disclosed. The preparation method of the catalyst includes: the mixture of salt and alkali solution is nucleated momentarily by nucleation/crystallization isolation method, preparing the composite metal hydroxide $Cu_yMMg_4$-LDHs as precursor, which has typical hexagonal morphology of the double hydroxide; the precursor is topologically transformed by heat treatment to produce unsaturated oxide; the catalyst with $Cu_y$-$MMgO_x$ interface structure is prepared by separating and electronically modifying Cu particles. By adjusting the ratio of $Cu^{2+}/M^{3+}$ in LDHs, the electronic and geometric structure of $Cu_y$-$MMgO_x$ interface can be flexibly controlled, thus enhancing the reaction activity, product selectivity and stability. The catalyst can be used in the selective hydrogenation of various alkynes in the fields of petrochemical and fine chemical industry, with the outstanding catalytic activity and C=C double bond selectivity. The catalyst also has good reusability.

4 Claims, 6 Drawing Sheets

$Cu_y/MMGO_x$ INTERFACIAL CATALYST FOR SELECTIVE ALKYNE HYDROGENATION AND ITS PREPARATION METHOD

BACKGROUND OF THE INVENTION

1. Field of the Invention

The invention is in the field of the petrochemical and fine chemical industry, and more particular for the stable $Cu_y/MMgO_x$ catalysts with controllable number and type of interface for selective alkynes hydrogenation and a preparation method thereof.

2. Description of Related Art

Ethylene, as an important raw material for polymers and petrochemical industries, is produced by naphtha cracking. The ethylene industry is the core of petrochemical productions, which produces more than 75% of petrochemical products and plays an important role in the national economy. At present, the method in industrial production of ethylene is steam cracking. However, in addition to ethylene, the pyrolysis products usually contain a small amount of acetylene, which is about 0.5-2.5%. Although the concentration of acetylene in the pyrolysis product is very low, in subsequent processing, especially in the ethylene polymerization process, it is easy to cause catalyst poisoning, then deactivation, which is not conducive to the industrial production of polyethylene, and even causes explosion accidents. It is therefore necessary to remove the content of acetylene from ethylene raw gas below 5 ppm. So far, the methods of removing trace acetylene from polyethylene raw gas include solvent extraction, acetylene copper precipitation, cryogenic distillation, catalytic hydrogenation and extra. Catalytic selective acetylene hydrogenation is the preferred purification method, since this process is not only simple in process and low in energy consumption, but also can improve ethylene production at the same time compared with other methods. However, after hydrogenation of acetylene to ethylene, ethane will continue to be formed, and other polymers such as green oil formed by acetylene polymerization will cover the active sites on the surface of the catalyst, resulting in the deactivation. Therefore, it is very difficult to control the selectivity of this reaction.

Because of the high activity in mild reaction, precious metal Pd is usually considered to be the most effective hydrogenation active component in industry, but ethylene is not easy to desorb on the surface of its catalyst, which further hydrogenates to produce ethane, showing poor selectivity. More importantly, the metal Pd content decreases in the world, leading to the increasing supply gap year by year and the rapidly rising price. Thus upon, effective substitution of precious metal is necessary. Non-precious mental Ni and Cu have certain activity in hydrogenation, among which the Ni-based catalyst is the earliest non-precious metal catalyst used in selective acetylene hydrogenation, but acetylene is prone to polymerization on the surface of Ni-catalyst to produce green oil, which will cover the active sites on the catalyst surface, leading to catalyst deactivation. As Cu has a semi-empty $4s$ orbit, the Cu-based catalyst shows excellent ethylene selectivity. However, the catalytic activity of Cu catalyst is far lower than that of Pd-based catalyst. In order to improve catalytic performance, researchers improve their catalytic activity, selectivity and stability by regulating the composition and structure of active components, selecting suitable carriers, and exploring new synthesis methods.

Wang et al. prepared a $Co@Cu/CoAlO_x$ interface catalyst with $CuCo_xAl_2$-LDHs as the precursor in the Interfacial Structure-Determined Reaction Pathway and Selectivity for 5-(Hydroxymethyl) furfural Hydrogenation over Cu-Based Catalysts, *ACS Catal.*, 10, 2, 1353-1365(2020). Some of the reduced super small Co clusters are distributed around Cu particles, forming Co—Cu interface. The catalyst catalyzes the hydrogenation of C=O and the hydrolysis of C—OH to produce up to 98.5% of DMF. Yi et al. deposited the unsaturated $FeO_x$ on the surface of $Pd/Al_2O_3$ catalyst to form $Pd/FeO_x$ interface for selective hydrogenation of 1,3-butadiene in Coating $Pd/Al_2O_3$ catalysts with $FeO_x$ enhances both activity and selectivity in 1,3-butadiene hydrogenation, *Chinese J. Catal.*, 38, 1581-1587(2017). The results show that $FeO_x$ receives electrons and isolates Pd atoms, forming small electron deficient Pd clusters, which greatly improves catalytic activity and olefin selectivity. It is worth noting that the above-mentioned metal-oxide interface structure catalyst ($N-MO_x$) is different from that of bimetallic catalyst, where two metal atoms are in the 0-valent metal state and arranged in the geometric way of alloy and core-shell. The reducible metal elements in the interface catalyst are only partially reduced, and the formed ultra-small $MO_x$ clusters are distributed around the metal N particles to form a heterogeneous interface structure, which can improve the catalytic rate and selectivity. However, although the traditional method to prepare the interface structure can improve the selectivity, it is difficult to accurately control the thickness of the species deposited on the surface of metal particles, being extremely easy to overburden the active sites, which seriously affects the catalytic activity.

Layered double hydroxides (LDHs) are a kind of two-dimensional layered materials with properties similar to manasseite. By using the structural topology effect of LDHs precursors, it is able to effectively control the degree of $MO_x$ migration and aggregation during interface structure construction, inhibiting the over encapsulation of metal particles, and thus obtain catalysts with metal-$MO_x$ interface structure. The interface effect can not only significantly change the electron structure through charge transfer, but also promote the geometric affinity, so that the activity of the catalyst and the selectivity of the target product can be achieved simultaneously at a single site. The invention uses the nucleation/crystallization isolation method to mix the salt and alkali solutions to achieve instantaneous nucleation, synthesizing the LDHs with controllable size of ecological particle via strengthening the crystal nucleation environment by regulating key parameters of the nucleation reactor, such as the stator rotor gap and rotation speed, etc. Taking LDHs as the precursor, the catalyst with the $Cu_y$-$MMgO_x$ interface structure is fabricated through the topotactic transformation in the process of heat treatment, producing unsaturated oxides, which separates and electronically modifies Cu particles, so as to realize the directional transformation of alkynes molecules to olefin molecules.

SUMMARY OF THE INVENTION

The purpose of the invention is to provide a $Cu_y/MMgO_x$ catalyst for selective alkyne hydrogenation and a preparation method thereof.

The catalyst provided by the invention is expressed as $Cu_y/MMgO_x$, where Cu is the active component; $MMgO_x$ is the carrier, and M represents one of the transition metals including Fe, Cr and V with reducibility, the better one is Fe; x represents the number of oxygen atoms in the carrier oxide, x=1~2.5; y is the ratio of Cu to metal M, being any integer between 1 and 8, preferably y=6, 7 or 8; the active metal component Cu is evenly dispersed on the surface of $MMgO_x$.

This catalyst uses $Cu_yMMg_4$-LDHs as the precursor. After topotactic transformation in the process of heat treatment, catalysts with a series of interfacial structure are obtained. Based on the structural topology effect of LDHs, while increasing the dispersion of active metal component Cu, the number of interface sites increases. The formed $MMgO_x$ can separate and electronically modify Cu particles, and effectively control the degree of migration and aggregation, inhibiting the over encapsulation of metal particles, so as to obtain $Cu_y$-$MMgO_x$ interface catalysts with the controllable electronic and geometric structure, type and quantity. This series of interfacial catalysts have higher conversion rate in acetylene selective hydrogenation, ethylene selectivity, and stability.

The preparation method of $Cu_y/MMgO_x$ catalyst for selective alkyne hydrogenation provided by the invention is as follows:

A. The mixed salt solution is prepared by dissolving Cu salt, Mg salt and M salt in 100 ml deionized water according to the metal ion molar ratio of 1~8/1~4/1, the total amount of three metal ions is 1.0~1.6 mol·$L^{-1}$; two kinds of alkali solutions are dissolved in deionized water to prepare alkali solution with concentration of 1.0~1.6 mol·$L^{-1}$;
 Cu salt comprises $Cu(NO_3)_2 \cdot 3H_2O$ or $CuCl_2$; Mg salt comprises $Mg(NO_3)_2 \cdot 6H_2O$ or $MgCl_2$; M salt is any one of them: $Fe(NO_3)_3 \cdot 9H_2O$, $FeCl_3$, $Cr(NO_3)_3 \cdot 9H_2O$, $CrCl_3$, $VCl_3$; Alkali solutions are any two of them: NaOH, KOH, $Na_2CO_3$ or $NaHCO_3$;

B. Turn on the nucleation reactor, set the stator-rotor gap of the reactor to be 0.1~0.5 mm and the rotation speed to be 100~3000 rpm, and transport the mixed salt solution and alkali solution in step A to the reactor at a rate of 0.5~2 mL·$min^{-1}$ by a peristaltic pump for nucleation, and control the total number of metal cations in the salt solution to be equal to the number of anions in the alkali solution; collect nucleation slurry at slurry outlet; Refer to patent No.: CN102616749b for the nucleation reactor;

C. The nucleation slurry is transferred to a reaction kettle and crystallized at 60~180° C. for 18~36 h. After naturally cooling down to ambient temperature, the crystallized products are centrifuged and washed to neutral with deionized water, and then dried at 50~80° C. for 24~36 h, obtaining the layered double hydroxides, namely $Cu_yFeMg_4$-LDHs precursor, where y is any integer between 1 and 8;

D. The $Cu_yFeMg_4$-LDHs obtained in step C is heated to 240~300° C. at a heating rate of 5~10° C.·$min^{-1}$ and calcined for 2~6 h, obtaining the corresponding mixed metal oxide of $Cu_yFeMg_4$-MMO, where y is any integer between 1 and 8;

E. The $Cu_yFeMg_4$-MMO obtained in step D is heated to 400~800° C. at a heating rate of 5~10° C.·$min^{-1}$ in an atmosphere of 10 vol. % $H_2/N_2$ and reduced for 4~6 h, After naturally cooling down to ambient temperature, 3 vol. % $O_2/N_2$ is introduced to passivate for 0.5~1 h, obtaining $Cu_y$-$MMgO_x$ interfacial catalyst, where y is any integer between 1 and 8; x is any number between 1 and 2.5.

The characteristics of the preparation method are as follows: the mixture of salt and alkali solution is nucleated momentarily by nucleation/crystallization isolation method, synthesizing the layer double hydroxides (LDHs) with controllable size of ecological particle via strengthening the crystal nucleation environment by regulating key parameters of the nucleation reactor, such as the stator rotor gap and rotation speed, etc. Taking LDHs as the precursor, the catalyst with the $Cu_y$-$MMgO_x$ interface structure is fabricated through the topotactic transformation in the process of heat treatment, producing unsaturated oxides, which separates and electronically modifies Cu particles, thus obtaining the catalyst with the $Cu_y$-$MMgO_x$ interface structure. The present preparation method works without using surfactant.

The prepared active metal components are uniformly dispersed on the surface of the carrier. By adjusting the ratio of $Cu^{2+}/M^{3+}$ in LDHs, the transition metals at the $Cu_y$-$MMgO_x$ interface are in the state of electron enrichment and have good stability, solving the problem that the thickness of the coating layer is difficult to accurately control due to the traditional methods, which leads to overburdening active sites. The catalyst can be used in the selective hydrogenation of various alkynes, with the outstanding catalytic activity and C=C double bond selectivity. The catalyst also has good reusability.

DETAILED DESCRIPTION OF EXEMPLARY EMBODIMENTS

Figure 1:
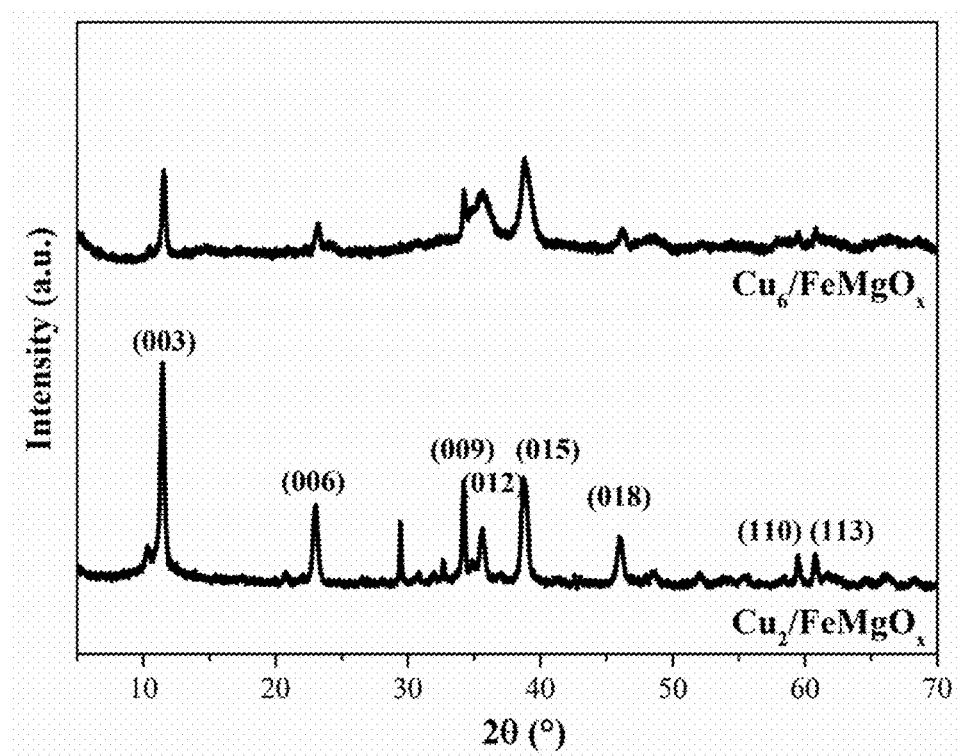
FIG. 1 shows the X-ray diffraction (XRD) results of the catalyst precursor $Cu_2FeMg_4$-LDHs prepared in embodiment 1.

As shown in FIG. 1, LDHs with good crystal structure have been successfully prepared.

Figure 2:
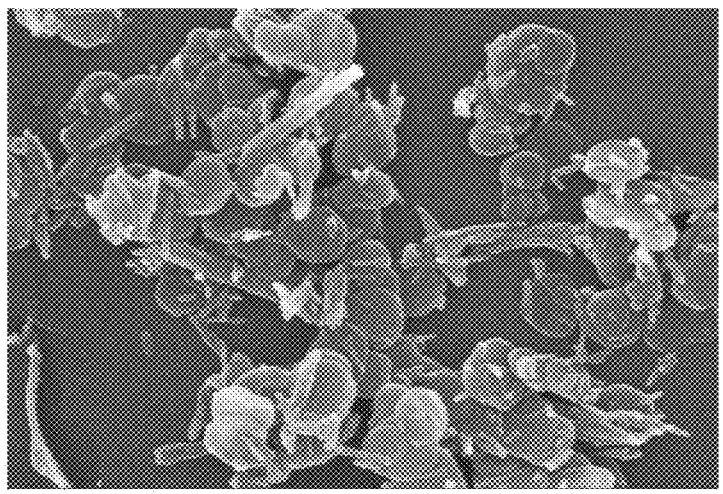
FIG. 2 shows the SEM image of the catalyst precursor $Cu_2FeMg_4$-LDHs LDHs prepared in embodiment 1.

FIG. 2 is a scanning electron microscope (SEM) image of the catalyst precursor composite metal hydroxide $Cu_2FeMg_4$-LDHs prepared in embodiment 1. From the SEM image, it can be seen that the LDHs are hexagonal.

Figure 3:
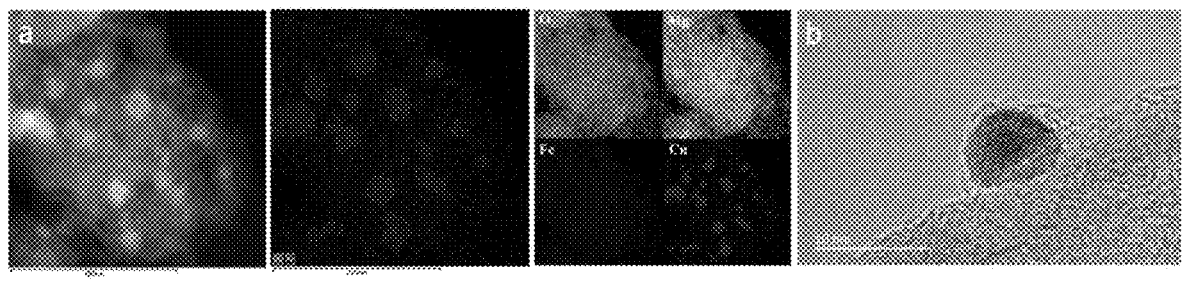
FIG. 3 shows the HRTEM and its mapping figure of $Cu_2/FeMgO_x$ catalyst prepared in embodiment 1. A is at the scale of 250 nm and B is the local amplification of A.

FIG. 3 shows the HRTEM and its mapping figure of $Cu_2/FeMgO_x$ catalyst prepared in embodiment 1. A is at the scale of 250 nm and B is the local amplification of A. It can be seen that the active metal components are uniformly dispersed on the surface of the carrier, and the Cu-$MMgO_x$ interface structure is formed.

Figure 4:
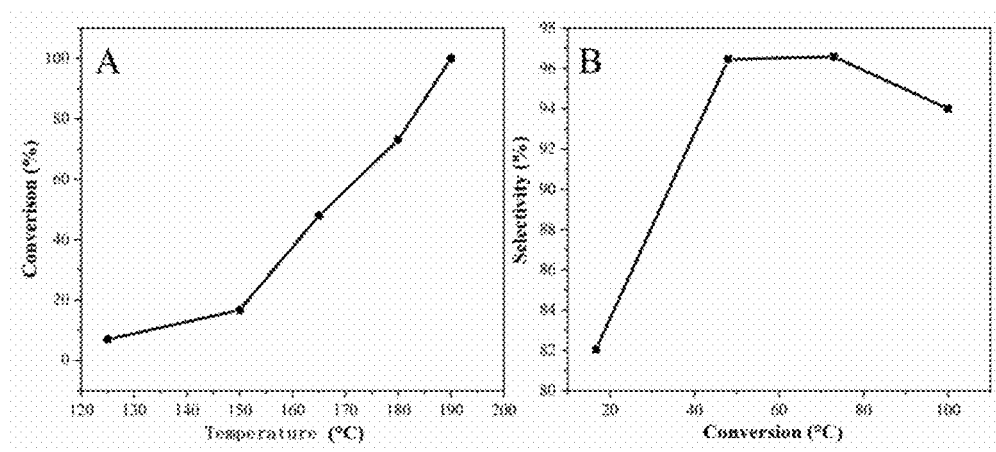
FIG. 4 shows the experimental results of $Cu_2/FeMgO_x$ catalyst prepared in embodiment 1 in selective acetylene hydrogenation. A shows the curve of acetylene conversion versus temperature, B shows the curve of ethylene selectivity versus acetylene conversion.

FIG. 4 shows the experimental results of $Cu_2/FeMgO_x$ catalyst prepared in embodiment 1 in selective acetylene hydrogenation. A shows the curve of acetylene conversion versus temperature, B shows the curve of ethylene selectivity versus acetylene conversion. When the reaction temperature is 225° C., the acetylene conversion is close to 100%, and the ethylene selectivity is 92%.

Figure 5:
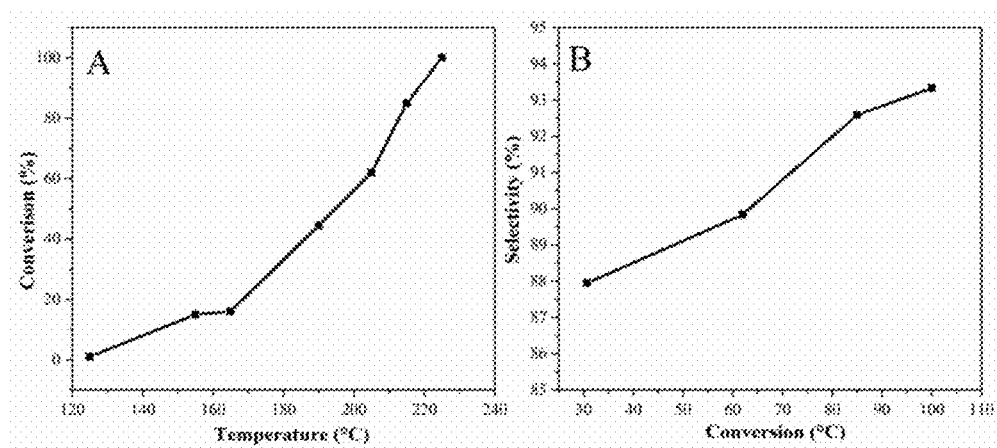
FIG. 5 shows the experimental results of $Cu_6/FeMgO_x$ catalyst prepared in embodiment 2 in selective acetylene hydrogenation. A shows the curve of acetylene conversion versus temperature, B shows the curve of ethylene selectivity versus acetylene conversion.

FIG. 5 shows the experimental results of $Cu_6/FeMgO_x$ catalyst prepared in embodiment 2 in selective acetylene hydrogenation. A shows the curve of acetylene conversion versus temperature, B shows the curve of ethylene selectivity versus acetylene conversion. When the reaction temperature is 190° C., the acetylene conversion is close to 100%, and the ethylene selectivity is 94%.

Figure 6:
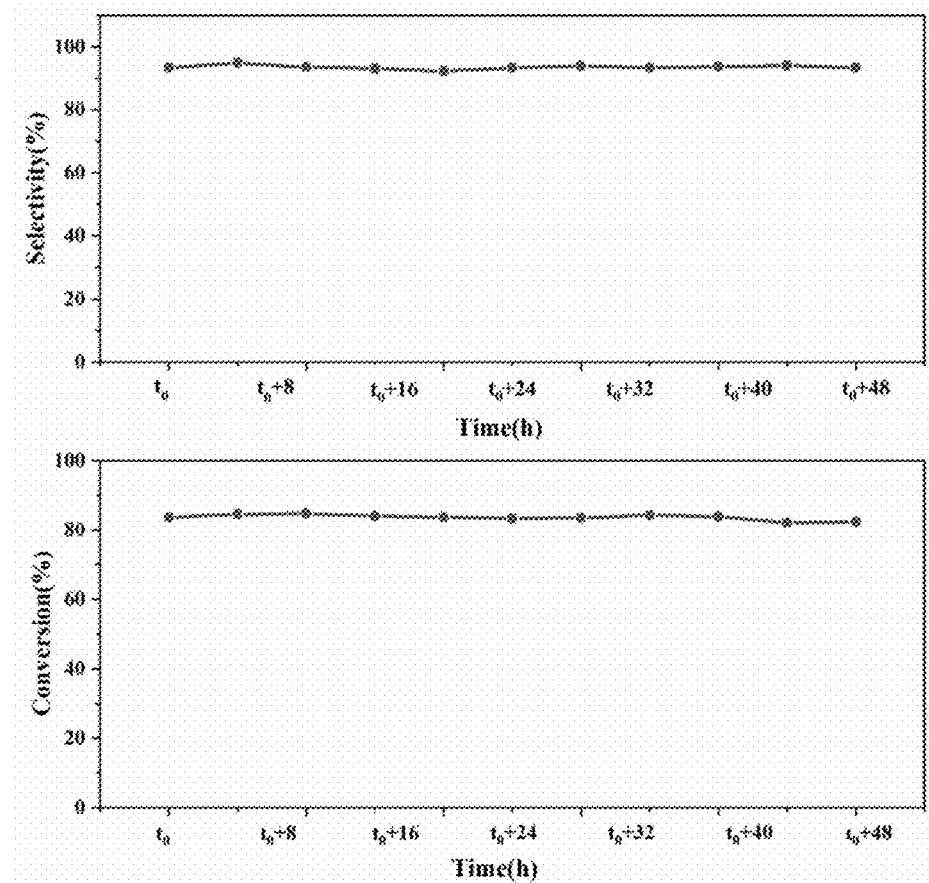
FIG. 6 shows the stability curve of $Cu_6/FeMgO_x$ catalyst prepared in embodiment 2 in acetylene selective hydrogenation.

FIG. 6 shows the stability curve of $Cu_6/FeMgO_x$ catalyst prepared in embodiment 2 in selective acetylene hydrogenation. The catalyst reacts continuously for 40 h, and collects a sampling point every 8 h. The conversion of acetylene is 85% and the selectivity of ethylene is 94%±3%, no significant change.

Embodiment 1

A. Dissolve 6.90 g $Cu(NO_3)_2.3H_2O$, 5.77 g $Fe(NO_3)_3.9H_2O$ and 14.65 g $Mg(NO_3)_2.6H_2O$ in 100 ml deionized water to prepare mixed salt solution; dissolve 6.40 g NaOH and 3.03 g $Na_2CO_3$ in 100 ml deionized water to prepare alkali solution;

B. Turn on the nucleation reactor, set the stator-rotor gap of the reactor to be 0.2 mm and the rotation speed to be 3000 rpm, and transport 100 ml mixed salt solution and 100 ml alkali solution in step A to the reactor at the rate of 1.5 mL·min$^{-1}$ by a peristaltic pump for nucleation; collect nucleation slurry at slurry outlet;

C. The nucleation slurry is transferred to a reaction kettle and crystallized at 120° C. for 24 h, after naturally cooling down to ambient temperature, the crystallized products are centrifuged and washed to neutral with deionized water, and then dried at 60° C. for 24 h, obtaining $Cu_2FeMg_4$-LDHs;

D. The $Cu_2FeMg_4$-LDHs obtained in step C is heated to 300° C. at a heating rate of 10° C.·min$^{-1}$ and calcined for 4 h, obtaining $Cu_2FeMg_4$-MMO;

E. The $Cu_2FeMg_4$-MMO obtained in step D is reduced at 500° C. at a heating rate of 2° C.·min$^{-1}$ in an atmosphere of 10 vol. % $H_2/N_2$ for 4 h. After naturally cooling down to ambient temperature, 3 vol. % $O_2/N_2$ is introduced to passivate for 0.5 h, obtaining $Cu_2$-$MMgO_x$ interfacial catalyst. The Cu/Fe ratio is 2/1.

The catalyst is used for selective acetylene hydrogenation:

The 200 mg catalyst is mixed with 1.9 g quartz sand with particle size of 40-70 mesh. The catalyst mixture or catalyst is filled in a quartz reaction tube with a diameter of 8 mm. The sample is activated in 5 vol. % $H_2/N_2$ mixture for 2 h before reaction, and then cooled to room temperature naturally. The temperature of catalyst performance test is 120-250° C. The gas composition of the reaction feed gas is 0.33% acetylene/1.02% hydrogen/32.86% ethylene/nitrogen balance gas. The test pressure is 4 bar and the airspeed is 10032 h$^{-1}$. The composition and content of reactants and products are analyzed by gas chromatography, and the data processing method is unified method. To ensure the test accuracy, the results are recorded after reaching the specified temperature for 25 minutes. The test is conducted in three groups, and the average value is the catalytic performance data at this temperature. The results are shown in FIG. 4.

Embodiment 2

A. Dissolve 13.18 g $Cu(NO_3)_2.3H_2O$, 3.67 g $Fe(NO_3)_3.9H_2O$ and 9.32 g $Mg(NO_3)_2.6H_2O$ in 100 ml deionized water to prepare mixed salt solution; dissolve 6.40 g NaOH and 1.93 g $Na_2CO_3$ in 100 ml deionized water to prepare alkali solution;

B. Turn on the nucleation reactor, set the stator-rotor gap of the reactor to be 0.2 mm and the rotation speed to be 3000 rpm, and transport 100 ml mixed salt solution and 100 ml alkali solution in step A to the reactor at the rate of 1.5 mL·min$^{-1}$ by a peristaltic pump for nucleation; collect nucleation slurry at slurry outlet;

C. The nucleation slurry is transferred to a reaction kettle and crystallized at 120° C. for 24 h, after naturally cooling down to ambient temperature, the crystallized products are centrifuged and washed to neutral with deionized water, and then dried at 60° C. for 24 h, obtaining $Cu_6FeMg_4$-LDHs;

D. The $Cu_2FeMg_4$-LDHs obtained in step C is heated to 300° C. at a heating rate of 10° C.·min$^{-1}$ and calcined for 4 h, obtaining $Cu_6FeMg_4$-MMO;

E. The $Cu_2FeMg_4$-MMO obtained in step D is reduced at 500° C. at a heating rate of 2° C.·min$^{-1}$ in an atmosphere of 10 vol. % $H_2/N_2$ for 4 h. After naturally cooling down to ambient temperature, 3 vol. % $O_2/N_2$ is introduced to passivate for 0.5 h, obtaining $Cu_2$-$MMgO_x$ interfacial catalyst. The Cu/Fe ratio is 6/1.

The prepared catalyst is used for selective acetylene hydrogenation: the reaction conditions are the same as those in embodiment 1, The results of catalytic performance are shown in FIG. 5-6.

Embodiment 3

A. Dissolve 13.18 g $Cu(NO_3)_2.3H_2O$, 3.64 g $Cr(NO_3)_3.9H_2O$ and 9.32 g $Mg(NO_3)_2.6H_2O$ in 100 ml deionized water to prepare mixed salt solution; dissolve 8.98 g KOH and 1.93 g $Na_2CO_3$ in 100 ml deionized water to prepare alkali solution;

B. Turn on the nucleation reactor, set the stator-rotor gap of the reactor to be 0.2 mm and the rotation speed to be 3000 rpm, and transport 100 ml mixed salt solution and 100 ml alkali solution in step A to the reactor at a rate of 1.0 mL·min$^{-1}$ by a peristaltic pump for nucleation; collect nucleation slurry at slurry outlet;

C. The nucleation slurry is transferred to a reaction kettle and crystallized at 120° C. for 24 h, after naturally cooling down to ambient temperature, the crystallized products are centrifuged and washed to neutral with deionized water, and then dried at 60° C. for 24 h, obtaining $Cu_6CrMg_4$-LDHs;

D. The $Cu_6CrMg_4$-LDHs obtained in step C is heated to 300° C. at a heating rate of 10° C.·min$^{-1}$ and calcined for 4 h, obtaining $Cu_6CrMg_4$-MMO;

E. The $Cu_6CrMg_4$-MMO obtained in step D is reduced at 500° C. at a heating rate of 5° C.·min$^{-1}$ in an atmosphere of 10 vol. % $H_2/N_2$ for 4 h. After naturally cooling down to ambient temperature, 3 vol. % $O_2/N_2$ is introduced to passivate for 0.5 h, obtaining $Cu_6$—$CrMgO_x$ interfacial catalyst. The Cu/Fe ratio is 6/1.

Embodiment 4

A. Dissolve 13.18 g $Cu(NO_3)_2.3H_2O$, 1.43 g $VCl_3$ and 9.32 g $Mg(NO_3)_2.6H_2O$ in 100 ml deionized water to prepare mixed salt solution; dissolve 6.40 g NaOH and 1.53 g $NaHCO_3$ in 100 ml deionized water to prepare alkali solution;

B. Turn on the nucleation reactor, set the stator-rotor gap of the reactor to be 0.2 mm and the rotation speed to be 3000 rpm, and transport 100 ml mixed salt solution and 100 ml alkali solution in step A to the reactor at a rate of 2.0 mL·min$^{-1}$ by a peristaltic pump for nucleation; collect nucleation slurry at slurry outlet;

C. The nucleation slurry is transferred to a reaction kettle and crystallized at 120° C. for 24 h, after naturally cooling down to ambient temperature, the crystallized products are centrifuged and washed to neutral with deionized water, and then dried at 60° C. for 24 h, obtaining Cu$_6$VMg$_4$-LDHs;

D. The Cu$_6$VMg$_4$-LDHs obtained in step C is heated to 300° C. at a heating rate of 10° C.·min$^{-1}$ and calcined for 4 h, obtaining Cu$_6$VMg$_4$-MMO;

E. The Cu$_6$CrMg$_4$-MMO obtained in step D is reduced at 600° C. at a heating rate of 5° C.·min$^{-1}$ in an atmosphere of 10 vol. % H$_2$/N$_2$ for 4 h. After naturally cooling down to ambient temperature, 3 vol. % O$_2$/N$_2$ is introduced to passivate for 0.5 h, obtaining Cu$_6$—VMgO$_x$ interfacial catalyst. The Cu/V ratio is 6/1.

Embodiment 5

A. Dissolve 13.18 g Cu(NO$_3$)$_2$.3H$_2$O, 3.67 g Fe(NO$_3$)$_3$.9H$_2$O and 9.32 g Mg(NO$_3$)$_2$.6H$_2$O in 100 ml deionized water to prepare mixed salt solution; dissolve 1.93 g Na$_2$CO$_3$ and 1.53 g NaHCO$_3$ in 100 ml deionized water to prepare alkali solution;

B. Turn on the nucleation reactor, set the stator-rotor gap of the reactor to be 0.3 mm and the rotation speed to be 2000 rpm, and transport 100 ml mixed salt solution and 100 ml alkali solution in step A to the reactor at a rate of 2.0 mL·min$^{-1}$ by a peristaltic pump for nucleation; collect nucleation slurry at slurry outlet;

C. The nucleation slurry is transferred to a reaction kettle and crystallized at 120° C. for 18 h, after naturally cooling down to ambient temperature, the crystallized products are centrifuged and washed to neutral with deionized water, and then dried at 60° C. for 24 h, obtaining Cu$_6$FeMg$_4$-LDHs-120;

D. The Cu$_6$FeMg$_4$-LDHs-120 obtained in step C is heated to 300° C. at a heating rate of 10° C.·min$^{-1}$ and calcined for 4 h, obtaining Cu$_6$FeMg$_4$-MMO-120;

E. The Cu$_6$FeMg$_4$-MMO-120 obtained in step D is reduced at 500° C. at a heating rate of 5° C.·min$^{-1}$ in an atmosphere of 10 vol. % H$_2$/N$_2$ for 4 h. After naturally cooling down to ambient temperature, 3 vol. % O$_2$/N$_2$ is introduced to passivate for 0.5 h, obtaining Cu$_6$—FeMgO$_x$-120 interfacial catalyst. The Cu/Fe ratio is 6/1.

Embodiment 6

A. Dissolve 13.18 g Cu(NO$_3$)$_2$.3H$_2$O, 3.67 g Fe(NO$_3$)$_3$.9H$_2$O and 9.32 g Mg(NO$_3$)$_2$.6H$_2$O in 100 ml deionized water to prepare mixed salt solution; dissolve 6.40 g NaOH and 1.93 g Na$_2$CO$_3$ in 100 ml deionized water to prepare alkali solution;

B. Turn on the nucleation reactor, set the stator-rotor gap of the reactor to be 0.4 mm and the rotation speed to be 3500 rpm, and transport 100 ml mixed salt solution and 100 ml alkali solution in step A to the reactor at a rate of 0.5 mL·min$^{-1}$ by a peristaltic pump for nucleation; collect nucleation slurry at slurry outlet;

C. The nucleation slurry is transferred to a reaction kettle and crystallized at 100° C. for 36 h, after naturally cooling down to ambient temperature, the crystallized products are centrifuged and washed to neutral with deionized water, and then dried at 60° C. for 24 h, obtaining Cu$_6$FeMg$_4$-LDHs-100;

D. The Cu$_6$FeMg$_4$-LDHs-100 obtained in step C is heated to 300° C. at a heating rate of 10° C.·min$^{-1}$ and calcined for 4 h, obtaining Cu$_6$FeMg$_4$-MMO-100;

E. The Cu$_6$FeMg$_4$-MMO-100 obtained in step D is reduced at 400° C. at a heating rate of 4° C. min$^{-1}$ in an atmosphere of 10 vol. % H$_2$/N$_2$ for 4 h. After naturally cooling down to ambient temperature, 3 vol. % O$_2$/N$_2$ is introduced to passivate for 1 h, obtaining Cu$_6$—FeMgO$_x$-100 interfacial catalyst. The Cu/Fe ratio is 6/1.

What is claimed is:

1. A method for preparing Cu$_y$/MMgO$_x$ interfacial catalyst for selective alkyne hydrogenation comprising the following steps:

A. Prepare the mixed salt solution by dissolving Cu salt, Mg salt and M salt in 100 ml deionized water according to the metal ion molar ratio of 1~8/1~4/1, the total amount of three metal ions is 1.0~1.6 mol·L$^{-1}$; two kinds of alkali solutions are dissolved in deionized water to prepare alkali solution with concentration of 1.0~1.6 mol·L$^{-1}$;
   Cu salt comprises Cu(NO$_3$)$_2$.3H$_2$O or CuCl$_2$; Mg salt comprises Mg(NO$_3$)$_2$.6H$_2$O or MgCl$_2$; M salt is any one of Fe(NO$_3$)$_3$.9H$_2$O, FeCl$_3$, Cr(NO$_3$)$_3$.9H$_2$O, CrCl$_3$, VCl$_3$; alkali solutions are any two of NaOH, KOH, Na$_2$CO$_3$ or NaHCO$_3$;

B. Turn on the nucleation reactor, set the stator-rotor gap of the reactor to be 0.1~0.5 mm and the rotation speed to be 100~3000 rpm, and transport the mixed salt solution and alkali solution in step A to the reactor at a rate of 0.5~2 mL·min$^{-1}$ by a peristaltic pump for nucleation, and control the total number of metal cations in the salt solution to be equal to the number of anions in the alkali solution; collect nucleation slurry at slurry outlet;

C. The nucleation slurry is transferred to a reaction kettle and crystallized at 60~180° C. for 18~36 h; after naturally cooling down to ambient temperature, the crystallized products are centrifuged and washed to neutral with deionized water, and then dried at 50~80° C. for 24~36 h, obtaining the layered double hydroxides (LDHs), namely Cu$_y$MMg$_4$-LDHs precursor, where y is any integer between 1 and 8;

D. The Cu$_y$MMg$_4$-LDHs precursor obtained in step C is heated to 240~300° C. at a heating rate of 5~10° C.·min$^1$ and calcined for 2~6 h, obtaining the corresponding mixed metal oxide of Cu$_y$MMg$_4$-MMO, where y is any integer between 1 and 8;

E. The Cu$_y$MMg$_4$-MMO obtained in step D is reduced at 400~800° C. at a heating rate of 5~10° C.·min$^1$ in an atmosphere of 10 vol. % H$_2$/N$_2$ for 4~6 h; after naturally cooling down to ambient temperature, 3 vol. % O$_2$/N$_2$ is introduced to passivate for 0.5~1 h, obtaining Cu$_y$-MMgO$_x$ interfacial catalyst, where y is any integer between 1 and 8; x is any number between 1 and 2.5.

2. The method for preparing Cu$_y$/MMgO$_x$ interfacial catalyst for selective hydrogenation of alkyne of claim 1, wherein the metal ion molar ratio of Cu, Mg, M in the mixed salt solution in step A is 6~8/4/1; M salt is Fe(NO$_3$)$_3$.9H$_2$O or FeCl$_3$; y in step C and E is 6, 7 or 8.

3. A Cu$_y$/MMgO$_x$ interfacial catalyst prepared according to the method of claim 1, wherein Cu is the active component, MMgO$_x$ is the carrier, and M represents one of the reducible transition metals: Fe, Cr and V; x is the number of oxygen atoms in the carrier oxide, x=1~2.5; y is the ratio of Cu to metal M, being any integer between 1 and 8; the active metal component Cu was uniformly dispersed on the surface of MMgO$_x$.

4. The $Cu_y/MMgO_x$ interfacial catalyst of claim 3, wherein M represents Fe, y is 6, 7 or 8.

* * * * *